United States Patent [19]

Bastioli et al.

[11] Patent Number: 5,262,458
[45] Date of Patent: Nov. 16, 1993

[54] BIODEGRADABLE ARTICLES BASED ON STARCH AND PROCESS FOR PRODUCING THEM

[75] Inventors: Catia Bastioli, Novara; Vittorio Bellotti, Fontaneto d'Agogna; Luciano del Giudice, Milan; Gianfranco del Tredici, Sesto Calende; Roberto Lombi; Angelos Rallis, both of Novara, all of Italy

[73] Assignee: Novamont S.p.A., Milan, Italy

[21] Appl. No.: 613,506

[22] PCT Filed: Mar. 8, 1990

[86] PCT No.: PCT/EP90/00375
§ 371 Date: Nov. 5, 1990
§ 102(e) Date: Nov. 5, 1990

[87] PCT Pub. No.: WO90/10671
PCT Pub. Date: Sep. 20, 1990

[30] Foreign Application Priority Data

Mar. 9, 1989 [IT] Italy ................. 41002 A/89
Aug. 2, 1989 [IT] Italy ................. 67666 A/89

[51] Int. Cl.⁵ .................................. C08L 3/00
[52] U.S. Cl. .......................... 524/52; 523/128
[58] Field of Search ................. 523/128; 524/52

[56] References Cited

U.S. PATENT DOCUMENTS

| | | | |
|---|---|---|---|
| 3,652,542 | 3/1972 | Hjermstad | 260/233.3 |
| 4,133,784 | 1/1979 | Otey et al. | 524/52 |
| 4,337,181 | 6/1982 | Otey et al. | 524/47 |
| 4,454,268 | 6/1984 | Otey et al. | 524/52 |
| 4,673,438 | 6/1987 | Wittwer | 106/126 |

FOREIGN PATENT DOCUMENTS

| | | |
|---|---|---|
| 0032802 | 7/1981 | European Pat. Off. . |
| 0282451 | 9/1988 | European Pat. Off. . |
| 0298920 | 1/1989 | European Pat. Off. . |
| 0304401 | 2/1989 | European Pat. Off. . |
| 0326517 | 8/1989 | European Pat. Off. . |
| 0327505 | 8/1989 | European Pat. Off. . |
| 0391853 | 10/1990 | European Pat. Off. . |
| 0404723 | 12/1990 | European Pat. Off. . |
| 0404727 | 12/1990 | European Pat. Off. . |
| 0404728 | 12/1990 | European Pat. Off. . |
| 0407350 | 1/1991 | European Pat. Off. . |
| 0408501 | 1/1991 | European Pat. Off. . |
| 0408502 | 1/1991 | European Pat. Off. . |
| 0408503 | 1/1991 | European Pat. Off. . |
| 0409781 | 1/1991 | European Pat. Off. . |
| 0409782 | 1/1991 | European Pat. Off. . |
| 0409783 | 1/1991 | European Pat. Off. . |
| 0409788 | 1/1991 | European Pat. Off. . |
| 0409789 | 1/1991 | European Pat. Off. . |
| 2190093 | 11/1987 | United Kingdom . |
| 8802313 | 2/1988 | United Kingdom . |

OTHER PUBLICATIONS

Chemical Abstracts, vol. 7, No. 8, p. 47, Abstract No. 60151n, F. H. Otey et al., "Starch-based blown films" (Aug. 24, 1987).

Otey, F. H. et al., Ind. Eng. Chem. Res. 26(8):1659–63 (1987), "Starch-Based Blown Films".

*Primary Examiner*—Paul R. Michl
*Assistant Examiner*—LaVonda DeWitt
*Attorney, Agent, or Firm*—Elizabeth M. Barnhard

[57] ABSTRACT

Formed articles comprising destructurized starch, an ethylene-acrylic acid copolymer and a product of the interaction of starch and ethylene-acrylic acid copolymer wherein the starch not bound to the copolymer is in the form of particles having sizes below 1 micron. The water content of such articles is lower than the one usually present in the starch. Said formed articles can also contain urea in an amount no higher than 30% by weight and/or ammonia in an amount not higher than 0.5% by weight. The process for obtaining such articles comprises the steps of extruding starch, an ethylene-acrylic acid copolymer and optionally water, urea and-/or ammonia at a temperature ranging from 90° to 150° C., reducing the water content to values lower than 6% by weight and injection molding or extrusion blowing the resulting composition.

22 Claims, No Drawings

BIODEGRADABLE ARTICLES BASED ON STARCH AND PROCESS FOR PRODUCING THEM

The present invention relates to biodegradable formed articles and films based on starch and to a process for producing them.

The term "formed articles", whenever used in the present description and in the claims, includes all the products having a thickness higher than 0.2 mm, such as boxes, containers in general, plates, packing articles, rods and the like.

In the latest years, several attempts have been made to produce biodegradable articles.

Among the various materials which have been suggested for producing formed articles and films, starches are no doubt, the most desirable ones, as they are natural, inexpensive and fully biodegradable products, which are widely available in nature.

U.S. Pat. No. 4,591,475 describes an injection molding process starting from non-destructurized starch. In this case, a high process instability was observed due to the fact that the viscosity of the product in the molten state was depending on the shear strain rate, wherefore the molding process is strictly depending on conditions such as screw speed, temperature, pressure and/or water content, and worsens the quality of the obtained articles.

In published European patent application No. 304,401, a process for the injection molding of capsules starting from destructurized starch is described. The articles obtained by means of this process, however, exhibit poor mechanical properties, besides being highly water-soluble.

It has been also suggested to combine the starch with other materials in order to produce articles endowed with satisfactory characteristics. Polyethylene is the material usually proposed to the purpose. The various attempts, which have been made to produce formed articles starting from starch-polyethylene mixes, have not given, however, satisfactory results. In fact, the products appear shapeless and weak because of the presence of several voids due to the conversion of humidity to vapour during the molding process. Furthermore, the resulting products have touch properties like those of paper.

U.S. Pat. No. 4,133,784 described compositions, which consist of starch and of an ethylene-acrylic acid copolymer (EAA), which are suitable for being transformed into films, and are flexible, water-resistant, thermoweldable and biodegradable.

Said compositions are transformed into films by means of techniques such as casting, simple extrusion or milling. However, these processes are slow and very expensive. Furthermore, at certain starch contents, as are necessary to obtain the desired mechanical properties, the biodegradability degree and the ultraviolet-ray stability of the products are strongly impaired.

On the other hand, the several attempts made by the Applicant in order to mold these compositions by injection were not successful due to the poor physico-mechanical properties of the products obtained; in fact, products exhibiting a low rigidity and a high elongation under load were obtained.

U.S. Pat. No. 4,337,181 proposed to add a sufficient amount of a neutralizing agent, such as ammonia or an amine, to the starch-EAA copolymer composition, in order to neutralize a part of all of the acid groups of EAA, and then to blow mold the resulting formulation with a humidity content ranging from 2 to 10%.

The addition of a neutralizing agent permits to overcome some drawbacks depending on the low rigidity of the products obtained remain or increase.

In Ind. Eng. Chem. Res. 1987, 26, pages 1659–1663 it was also proposed to add urea and/or polyols to the starch-EAA copolymer compositions in order to favor the preparation and to improve the economic and qualitative features of the resulting films. The effect of the presence of the urea is to enable the crystalline structure of the starch to be destroyed by small quantities of water and hence to enable granules for filming to be produced directly from a composition with a water content of around 16%, as well as of eliminating the necessity to premix the starch-EAA copolymer mixture in a very complex mixer with a great water amount before the extrusion process. Therefore, also the addition of urea improves the process conditions of the starch-EAA copolymer mixture, while the poor physico-mechanical properties of the resulting products remain unchanged.

The Applicant has now found that formed articles produced by means of the injection molding technology and films produced by extrusion-blowing have excellent physical-mechanical properties, such as high break toughness, high flexural yield strength and a modulus by far higher than the one of the individual components, as well as water insolubility, when said articles and films contain the following three phases perfectly interpenetrated with one another:

(1) a phase of destructurized starch in the form of particles, each having an average number diameter lower than 1 micron;
(2) a phase of ethylene-acrylic acid copolymer (EAA);
(3) a phase consisting of an IPN (interpenetrated network) product resulting from the interaction between starch and ethylene-acrylic acid copolymer, and optionally
(4) water in an amount lower than 6%, preferably lower than 2% by weight with respect to the total composition.

The product of the interaction between starch and EAA copolymer is obtained in situ during the conversion process of the starting products to the formed article.

Preferably the ethylene-acrylic acid copolymer (EAA) has an acrylic acid content ranging from 3 to 30% by weight and the destructurized starch phase which is not bound to the EAA copolymer, is finely and uniformly dispersed in the mix in the form of particles having an average number diameter below 1 micron and a dispersion of the particles sizes below 3.

The dispersion of the destructurized starch particles dimensions is determined by the ratio between the average number diameter and the average surface diameter.

The proportion of the various components of the composition may vary as a function of the properties to be obtained, of the temperature and of the forming process. Generally, formed articles and films having excellent physical-mechanical characteristics and insolubility in water contain:

from 10 to 90% by weight of a total destructurized starch;
from 10 to 90% by weight of a total EAA copolymer having an acrylic acid content ranging from 3 to 30% by weight; and from 0 to 6% of water, wherein less than 40% and preferably, less than 20% by weight of the total starch is free and in the form of particles having an average number diameter below 1 micron, while the remaining starch is bound to the EAA copolymer to form said IPN product.

The formed articles and films, which are the object of the present invention, may also contain urea, which is added to the starting mix in order to improve the processability thereof. The urea amount, if any, does not exceed 30% by weight and preferably it ranges from 5 to 20% by weight referred to the mix.

The water content of the articles of the present invention is generally lower than the one which is generally present in the starch. Usually, the water content does not exceed 6% by weight and it may be also fully absent.

The ammonia, which is optionally added to the starting mix in order to improve the preparation of the composition is removed either during the extrusion process or subsequently, during a drying step, wherefore the articles of the present invention generally do not contain ammonia, or the ammonia content does not exceed, at the most, 0.5% by weight with respect to the mix.

The process for producing the formed articles and films which is another object of the present invention, comprises mixing the components of the mix containing starch, an EAA copolymer, in a starch/EAA copolymer weight ratio ranging from 1:9 to 9:1, water, and optionally urea and ammonia, in an extruder heated to a temperature ranging from 90° to 150° C., bringing the water content to a value below 6% by weight and the ammonia content to a value below 0.5% by weight.

The reduction of the water content prior to the further processing of the composition constitutes an important feature of the process according to the invention.

The reduction of the water content and optionally of the ammonia content can be carried out either by venting, directly in the extruder, or by drying at about 70°-100° C. in an air flow or under vacuum after the extrusion step.

According to a preferred method for the preparation of the formed articles and films of the present invention, the reduction of the water content is carried out in an intermediate degassing stage of the extrusion process.

Accordingly, this preferred method comprises supplying to an extruder heated to a temperature of between 90° and 150° C. a material including starch and an ethylene-acrylic acid copolymer in a starch/copolymer ratio of from 1:9 to 9:1, and a quantity of water of from 10 to 25% of the weight of the starch component, and subjecting the supplied material to the following sequence:

- a first stage in which the starch supplied is intimately mixed with the copolymer until it is substantially destructurized and interpenetrated,
- a stage in which the material output from the mixing step is degassed to reduce its water content to no more than 2% by weight of the weight of the composition, and
- a stage in which the degassed material is transported and compressed at a pressure greater than 500 kPa and the material is extruded at a temperature of between 105° and 130° C.

Upstream of the first mixing stage, the material supplied is preferably subjected to a transportation stage during which the temperature of material is increased progressively to between 60° and 100° C. The length of the transportation zone of the extruder is typically between 4 and 20 times the diameter of the extruder screw.

The subsequent mixing stage is carried out at a temperature preferably of between 105° and 140° C. under such conditions that the starch is at the same time substantially destructurized and interpenetrated with the copolymer. The mixing zone extends for a distance preferably between 4 and 20 times the diameter of the extruder screw and the material is subjected to shear deformation at a rate of between 50 and 5000 seconds$^{-1}$.

The phenomena which take place in this stage and which lead to the destructurization of the starch are known and are generally explained by the creation of disorder in the molecular structure of the starch particles as a result of heat treatment carried out above the glass-transition temperature and melting points of its components.

The degassing stage may typically include from 1 to 4 degassing zones in which the body of the extruder is brought to a subatmospheric pressure, generally between 690 and 700 mm Hg. In this stage, the quantity of water can be reduced to values of from 2 to 0.1%, preferably below 1%. The degassing is carried out with the use of one or more water ring pumps of known type.

The degassed material then goes through a further transportation stage constituted by conveyor elements alone, or by mixing elements followed by conveyor elements, to improve the interpenetration and prevent the blend from losing the uniformity achieved during the first mixing stage. The transportation zone generally extends for a distance of from 4 to 20 times the diameter of the extruder screw.

The fused material is then compressed to pressures greater than 500 kPa, preferably greater than 1500 kPa and more preferably greater than 3000 kPa, with compression ratios of between 1:1.5 and 1:4. The fused material is then extruded in the form of filaments or sheets at a temperature preferably of between 105° and 130° C.

The extruded sheet can be used for thermoforming either by the vacuum technique or by the male/female moulding technique. Granules or cubes can be produced from the extruded filament or sheet respectively and they may then be used for film-blowing at a temperature preferable of between 100° and 140° C. by conventional techniques or they may be used for injection moulding.

In particular, it has been found that the introduction of the degassing stage to reduce the water content to less than 2%, and more preferably to less than 1% by weight, between two mixing and transportation-compression stages carried out under conditions such as to destructurize the starch and obtaining an interpenetrated structure, provides an extrusion which is particularly suitable for subsequent processing by extrusion and blowing.

The film-blowing bubble is perfectly constant and the tubing produced has no problem with tackiness. Moreover, the modulus of films is increased and they can withstand strains and stresses greater than or equal to those withstood by the films described in U.S. Pat. No. 4,133,784 and U.S. Pat. No. 4,337,181 mentioned above.

Formed articles are obtained by injection molding the resulting composition at a temperature ranging from 130° to 180° C., preferably from 130° to 160° C. under a shear strain rate ranging from 1,000 to 10,000 sec$^{-1}$ and for a time ranging from 10 to 120 seconds, preferably 3–60 seconds depending on the desired article thickness.

Molding temperature and shear rate along with the ammonia content and the water content of the composition are the critical parameters of the process of the present invention, to obtain finished molded products endowed with the required characteristics.

In fact it was observed that if it is operated in such conditions it is possible to obtain destructurized starch particles uniformly dispersed in the matrix having an average number diameter below 1 micron, preferably ranging from 0.1 to 0.5 microns, and a particle size dispersion lower than 3, and the formation in situ of a product of the interaction between starch and EAA copolymer in such a proportion as to bind at least 60% and preferably from 80% to 100% of the total starting starch.

The formed articles of the present invention exhibit high physical-mechanical properties, such as a modulus higher than 5,000 kg/cm$^2$, a good tenacity to breaking; a high flexural yield strength of the order of 300–400 kg/cm$^2$, and are insoluble in water. Such articles exhibit a worsening of the physical-mechanical properties when they are dipped into water, but they retain their shape unchanged and do not exhibit any surface alteration; by reconditioning in air at 25° C. and 50% of relative humidity, such articles tend to become transparent and brittler.

The term "starch" whenever used in the present description and in the claims comprises in general all the starches of natural or vegetable origin, which are substantially composed of amylose and/or amylopectine. They are extractable from various plants such as, e.g. potato, rice, tapioca, maize and cereals such as rye, oats, wheat, etc.. The maize starch is preferred. The term "starch" includes also starch which is modified in order to lower the acid value within the range of from 3 to 6, as well as potato starch, in which the type and concentration of the cations associated with the phosphate group have been modified. Ethoxylated starches, acetate starches, cationic starches, oxidized starches, cross-linked starches, etc. may be used too in the process of the present invention.

Starch of natural origin is used as it is, without being dried beforehand, with its intrinsic bound water content which is of the order of 10–13% by weight. A quantity of water such as to bring the total water content to values no more that about 25% of the total weight of the dry starch, preferably to between 10 and 15%, is added to the starch in the extruder.

The EAA copolymer used in the method must contain a sufficient number of carboxyl groups to be compatible with the starch. The presence of the carboxyl groups also makes the copolymer dispersible in water. The preferred EAA copolymer is that produced by the copolymerisation of a mixture comprising from 3 to 30%, preferably 20% by weight of acrylic acid and, correspondingly, from 97 to 70%, preferably 20%, by weight of acrylic acid and, correspondingly, from 97 to 70%, preferably 80%, by weight of ethylene. The starch/EAA copolymer ratio is preferably between 1:4 and 4:1. Naturally, an increase in the starch content towards the higher values of the range given above is advantageous as regards the biodegradability of the films produced.

The addition of urea to the material supplied to the extruder has been found to be advantageous for facilitating the destructuring of the starch and making it compatible with the EAA copolymer. When it is present, the quantity of urea is no more than 30%, and preferably between 5 and 20%, by weight of the total composition.

To the starch-EAA copolymer it is possible to add, optionally, ammonia in a non-critical amount and generally up to 7% (30% saturated ammonia solution) wt. referred to the weight of the dry starch. The added ammonia is then completely or partially removed either during the extrusion of the composition or during the drying step or intermediate degassing step.

The finished products are characterized, in fact, by being susstantially free from ammonia, which in any case remains at very low levels, always lower than 0.5% by weight, preferably below 0.2%.

Also polyethylene may be added to the composition in order to improve the stability to ultraviolet rays of the finished product resulting therefrom.

Any type of polyethylene may be added, although low-density polyethylene is the one usually utilized to this end. The added polyethylene amount is generally lower than 40% of the mixture.

Other materials, either polymeric or monomeric, may be added to the compositions prior to the extrusion step. Thus, for example, polyvinyl alcohol may be added in variable amounts in order to modify the water behavior of the formed articles; UV-stabilizers, such as for example carbon black, may be added to improve the stability of the articles to sunlight; antiflame agents can be added in the case where the formed articles should be required to exhibit said property. Other additives comprise the conventional additives, which are generally incorporated in the molding compositions based on starch, such as fungicides, herbicides, antioxidants, fertilizers, opacifiers, stabilizers, plasticizers and the like. All these additives are utilizable in conventional amounts, as is known to those skilled in the art or as is easily determined by routine tests, and they can amount up to 20% by weight of the final composition.

The following example is given to better illustrate the present invention.

In the example, all percentages are percent by weight, unless otherwise specified.

EXAMPLE 1

A composition containing the following components was prepared:
37% by weight of starch Globe 3401 Cerestar having a water content of 11%
37% by weight of EAA copolymer 5981 produced by Dow Chemical, containing 20% of acrylic acid;
6.8% by weight of NH$_4$OH at 30%;
6.8% by weight of water; and
12.4% by weight of urea.

The products were premixed and then fed by a Licoarbo proportioning device DC-10 to a Baker Perkins extruder MPC/V-30. Such extruder consisted of a two-screw group divided into two portions. The screw diameter was equal to 30 mm and the screw length/diameter ratio (L/D) was equal to 10:1; the group being connected with a single-screw extruder press, having a capillary head and a screw of 38 mm diameter and a L/D equal to 8:1, divided into three portions. The utilized capillary head had a diameter of 4.5 mm.

The temperatures employed were 80° C. in the two portions of the two-screw group and 120°, 100° and 130° C., respectively, in the three portions of the single-screw extruder.

The operative conditions were as follows:
two-screw extruder revolutions: 250 r.p.m.
single-screw extruder revolutions: 110 r.p.m.
pressure in the chamber: <40 atm.

The extruded product was air-cooled and then granulated by an OMC granulator. The resulting mix was dried for 4 hours at 100° C. under vacuum before injection molding. The water content of the mix after drying was 0.3% and the ammonia content was lower than 0.1% by weight.

The dried mix was injection molded by means of a SANDRETTO press 57/60 with the two capillary tubes being symmetrically arranged on the bottom of the article to be molded.

The operative conditions were as follows:

| | |
|---|---|
| injection temperature: | 155°, 165°, 180° C. |
| mold temperature: | 25° C. |
| shear strain rate (sec$^{-1}$): | from 2000 to 6000 sec$^{-1}$ |
| total injection time: | 15 sec. |
| total cycle time: | 45 sec. |
| holding pressure: | 400 bar. |

The samples so obtained had a box-type shape, and a square truncated pyramidal geometry with dimensions of the smaller base equal to 60×60 mm and of the greater base equal to 67×67 mm, the height being 60 mm and the thickness 3 mm.

The elemental composition of the samples obtained was the following:
C=56.70%
H=9.55%
N=6.6%

The IR spectrum did not reveal the presence of ammonium salts as it indicated the absence of ammonia.

The sizes of the destructurized starch particles not bound to the EAA copolymer were measured by means of analysis under the transmission electron microscope (Philips EM 300) on little product chips obtained by means of an ultra-microtome (Nova LKB).

The average number diameter and average surface diameter were obtained starting from the particle sizes measured on micrographies enlarged by 6,000 and 10,000 times taken from different points of the sample.

In the product obtained, the average number diameter of the non-bound starch particles was equal to 0.44 microns. The ratio between average surface diameter and average number was taken as a measure of the particles dispersion. In the product obtained, said ratio was equal to 1.44.

The flexural characteristics, measured according to ASTM D 790 standard, were as follows:
Young modulus: 7,000 kg/cm$^2$
yield strength: 310 kg/cm$^2$
yield strain: 11%

The sample was left in water at 20° C. for 20 days and then it was allowed to condition for 1 month at room temperature and at a humidity of about 50%.

The centesimal analysis of the conditioned sample was as follows:
C=57,75%
H=9.8%
N=2.45%.

The average number diameter of the non-bound starch particles was equal to 0.36 microns and the particle dispersion was equal to 1.58.

The flexural characteristics measured according to ASTM D 790 standards were as follows:
Young modulus: 5,000 kg/cm$^2$
yield strength: 230 kg/cm$^2$
yield strain: 13%.

EXAMPLE 2

The following composition was supplied to a double-screwed extruder with a screw diameter of 50 mm and a screw length/diameter ratio of 36:
  4.0 kg of the starch GLOBE 03401 Cerestar which had not been dried beforehand,
  1.2 kg of urea,
  4.0 kg of the Dow Chemical copolymer EAA 5981 with a 20% acrylic acid content.
  0.6 liters of water.

The extruder included the following zones:
  a transportation zone: 4 diameters,
  a first mixing zone: 20 diameters,
  a degassing zone connected to a vacuum at a pressure of approximately 690 mm Hg,
  a transportation zone with mixing elements: 11 diameters,
  a compression zone with a compression ratio of 1:2.

The temperatures set were between 60° and 80° C. for the transportation zone and between 90° and 130° C. for the subsequent zones. The tests were carried out with screw rotation rates of between 100 and 250 rpm and a head pressure of 40 atm (4000 kPa).

The fused material was extruded with an output temperature of 120° C. and a water content of approximately 0.7%.

The extrusion, in the form of a filament, was pelletized and the pellets were supplied to a HAAKE extruder with a diameter of 19 mm and L/D of 25, provided with a film-blowing head. The extrusion and blowing process was carried out with screw rotation rates of from 30 to 65 rpm and a compression ratio of 1:2.

Rectangular test pieces for tensile testing according to ASTM 882 were formed from the films which were approximately 100 microns thick.

The test pieces were conditioned at 23°±1° C. and 55±5% relative humidity for 24 hours.

The mechanical strength tests gave the following results expressed as average values.
Young's modulus: 200 kg/cm$^2$
Breaking strain: 150%
Breaking stress: 150 kg/cm$^2$ In all the tests, the tubing produced during blowing had no problems of tackiness and the bubble was stable and constant.

Similar results were obtained when the same composition as that quoted above but including 6.0 liters of a 30% ammonia solution was added to the double-screwed extruder.

EXAMPLE 3

Pellets prepared as in Example 2 were supplied to an extruder with a diameter of 35 mm and an L/D of 20, provided with a flat head and rollers with internal water-cooling (cirrol).

The process for producing the film was carried out at a screw rotation rate of 40 rpm and a temperature of between 110° and 130° C. and with a compression ratio of 1:2.

The temperature of the cirrol was approximately 15° C.

It was thus possible to produce films with thicknesses of 20 to 299 μm by varying the collection speed. The tensile characteristics of the film tested according to ASTM standard 882 were:

|  | In the direction of extrusion | Perpendicular to the direction of extrusion |
| --- | --- | --- |
| Young's modulus | 2200 kg/cm$^2$ | 1500 kg/cm$^2$ |
| Breaking strain | 200% | 120% |
| Breaking stress | 140 kg/cm$^2$ | 115 kg/cm$^2$ |

EXAMPLE 4

Pellets prepared as in Example 1 were supplied to an extruder with:
a diameter of 50 mm,
an L/D=20,
a flat head approximately 70 cm wide.

The flat head of the type and for PP and PE had a torsion bar for ensuring that the output speed of the fused material was uniform at all points.

The conditions for the extrusion of a sheet 0.8 mm thick were as follows:
a temperature of 140° C. throughout the extruder,
screw rotation rate: 60 rpm,
head aperture: 1 mm.

The sheet was collected on a calendar with a stand of three water-cooled rolls.

The sheet thus obtained was formed in a male/female tray die with dimensions of 20 cm × 15 cm after the sheet had been heated to 80° C.

The tray thus obtained showed a uniform thickness.

We claim:

1. Articles based on Starch, insoluble in water, comprising:
   (1) a phase consisting of destructurized starch in the form of particles having an average number diameter below 1 micron;
   (2) a phase consisting of an ethylene-acrylic acid copolyner (EAA);
   (3) a phase consisting of an IPN (interpenetrated network) resulting from the interaction between starch and ethylene-acrylic acid copolymer and,
   (4) a water content in the range from 0 to 2% by weight calculated on the total weight of the three phases.

2. Articles based on starch according to claim 1, wherein said ethylene-acrylic acid copolymer has an acrylic acid content ranging from 3 to 30% by weight and the destructured starch phase which is not bound to the ethylene-acrylic acid copolymer, is finely and uniformly dispersed in the mix in the form of particles having an average number diameter below 1 micron and a dispersion of the particles sizes below 3.

3. Articles based on starch according to claim 1 comprising:
   from 10 to 90% by weight of a total ethylene-acrylic acid copolymer, having an acrylic acid content ranging from 3 to 30% by weight, and
   less than 2% by weight of water; wherein less than 40% and preferably less than 20% by weight of the total starch is free and in the form of particles having an average number diameter lower than 1 micron, the remaining starch being bound to the ethylene-acrylic acid copolymer to form said interaction product.

4. Articles based on starch according to claim 3, wherein from 80 to 100% of the total starch is bound to the ethylene-acrylic acid copolymer:

5. Articles based on starch according to claims 2 or 3, wherein the average number diameter if the particles ranges from 0.1 to 0.5 microns.

6. Articles based on starch according to claim 1, wherein the ethylene-acrylic acid copolymer has an acrylic acid content equal to 20% by weight.

7. Articles based on starch according to claim 1, preceding claims, wherein the water content ranges from 0 to 2% by weight referred to the mix.

8. Articles based on starch according to claim 1, containing, in addition, urea in an amount not exceeding 30% by the weight with respect to the mix.

9. Articles based on starch according to claim 1, containing, in addition, ammonia in amount not exceeding 0.5% by weight with respect to the mix.

10. Articles based on starch according to claim 1, containing polyethylene, polyvinyl alcohol and/or antioxidants, stabilizers, antiflame agents, fertilizers, opacifiers, plasticizers.

11. A process for producing starch-based articles comprising:
    supplying to a heated extruder a material including starch and an ethylene-acrylic acid copolymer in a starch/copolymer ratio of from 1:9 to 9:1, and a quantity of water of from 10 to 25% of the total weight of the starch component, and processing said material in the extruder which is heated to a temperature of from 90° and 150° C. according to a stage sequence comprising:
    a first mixing stage in which the starch supplied is intimately mixed with the copolymer to destructurize the starch and achieve interpenetration of the starch and copolymer phase,
    a stage in which the material output from the mixing step is degassed to reduce its water content to less than 2% of the weight of the composition,
    a transportation and compression stage in which the degassed material is transported and compressed to a pressure greater than 500 kPa and the material is extruded at a temperature of between 105° and 130° C.

12. A process according to claim 11 including a first transportation stage at a temperature of between 60° and 100° C. immediately upstream of the first mixing stage.

13. A process according to claim 11, in which the material supplied to the extruder is subjected to shear deformation at a rate of between 50 and 5000 seconds$^{-1}$ during the first mixing stage.

14. A process according to claim 11, in which the first mixing stage extends for a distance of 4 to 20 times the diameter of the extruder screw.

15. A process according to claim 11, in which the stage for the transportation of the degassed material extends for a distance of 4 to 20 times the diameter of the extruder screw and contains mixing elements which can prevent separation phenomena.

16. A process according to claim 11, in which a compression ratio of from 1:1.5 to 1:4 is applied in the compression stage.

17. A process according to claim 11, in which the starch material is selected from the group consisting of unmodified starches, modified starches, amylose and amylopectin.

18. A process according to claim 11, in which the material supplied to the extruder includes a quantity of ammonia of up to 7% of the weight of the dry starch, and in which the ammonia content is reduced to no more than 0.2% by weight of the weight of the extruded composition in the degassing stage.

19. A process according to claim 11, in which the material supplied to the extruder includes a quantity of urea up to 30% by weight of the composition.

20. A process according to claim 11, in which the starch and the copolymer are supplied to the extruder in a ratio of from 1:4 and 4:1.

21. A process according to claim 12, in which the material supplied to the extruder includes a quantity of water of from 10 to 15% of the weight of the dry starch component.

22. A process according to claim 11, for the production of molded articles wherein the extruded composition having a water content of less than 2% wt is injection molded at a temperature ranging from 130° to 180° C. under shear strain rates ranging from 1,000 and 10,000 sec$^{-1}$ and for a time ranging from 10 to 120 seconds, depending on the article thickness.

* * * * *